United States Patent
Lei et al.

(10) Patent No.: US 10,611,757 B2
(45) Date of Patent: Apr. 7, 2020

(54) CRYSTALLINE FORM OF CHEMICAL COMPOUND, AND PREPARATION METHOD, COMPOSITION, AND APPLICATION THEREOF

(71) Applicants: WUHAN LL SCIENCE AND TECHNOLOGY DEVELOPMENT CO., LTD., Wuhan, Hubei (CN); WUHAN QR PHARMACEUTICALS CO., LTD., Wuhan, Hubei (CN)

(72) Inventors: Sijun Lei, Hubei (CN); Xiang Fang, Hubei (CN); Yongkai Chen, Hubei (CN); Wei Feng, Hubei (CN); Chaodong Wang, Hubei (CN)

(73) Assignees: Wuhan LL Science and Technology Development Co., Ltd., Wuhan, Hubei (CN); Wuhan QR Pharmaceuticals Co., Ltd., Wuhan, Hubei (CN)

( * ) Notice: Subject to any disclaimer, the term of this patent is extended or adjusted under 35 U.S.C. 154(b) by 0 days.

(21) Appl. No.: 16/301,027

(22) PCT Filed: Jul. 10, 2017

(86) PCT No.: PCT/CN2017/092416
§ 371 (c)(1),
(2) Date: Nov. 13, 2018

(87) PCT Pub. No.: WO2018/010622
PCT Pub. Date: Jan. 18, 2018

(65) Prior Publication Data
US 2019/0177312 A1   Jun. 13, 2019

(30) Foreign Application Priority Data

Jul. 11, 2016 (CN) .......................... 2016 1 0539614

(51) Int. Cl.
| | | |
|---|---|---|
| C07D 413/14 | (2006.01) |
| A61P 9/12 | (2006.01) |
| A61P 9/06 | (2006.01) |
| A61K 31/4245 | (2006.01) |
| A61P 9/00 | (2006.01) |
| A61P 13/12 | (2006.01) |
| A61P 9/04 | (2006.01) |

(52) U.S. Cl.
CPC ........ *C07D 413/14* (2013.01); *A61K 31/4245* (2013.01); *A61P 9/00* (2018.01); *A61P 9/04* (2018.01); *A61P 9/06* (2018.01); *A61P 9/12* (2018.01); *A61P 13/12* (2018.01); *C07B 2200/13* (2013.01)

(58) Field of Classification Search
CPC .................................................. C07D 413/14
See application file for complete search history.

(56) References Cited

U.S. PATENT DOCUMENTS

| | | | |
|---|---|---|---|
| 9,708,306 B2 * | 7/2017 | Ge .................. A61K 31/4245 |
| 2014/0371279 A1 * | 12/2014 | Lei ...................... C07D 413/10 |
| | | | 514/364 |
| 2017/0022188 A1 * | 1/2017 | Ge .................. A61K 31/4245 |
| 2019/0202808 A1 * | 7/2019 | Priestley .............. C07D 401/14 |
| 2019/0314368 A1 * | 10/2019 | Liang .................. A61K 31/497 |

FOREIGN PATENT DOCUMENTS

| | | | | |
|---|---|---|---|---|
| CN | 103709154 A | | 4/2014 | |
| CN | 104774196 A | * | 7/2015 | |
| CN | 104774196 A | | 7/2015 | |
| CN | 105153141 A | | 12/2015 | |
| CN | 105237527 A | | 1/2016 | |
| CN | 107400122 A | * | 11/2017 | ........... C07D 413/14 |
| EP | 3447054 A1 | * | 2/2019 | ........... C07D 413/14 |
| EP | 3492466 A1 | * | 6/2019 | ............. A61K 31/42 |

OTHER PUBLICATIONS

W. B. White et al., Hypertension (2011) (Year: 2011).*
Solid State Characterization of Pharmaceuticals 63 (R.A. Storey et al., eds., 2011) (Year: 2011).*
A.J. Cruz-Cabeza et al., 44 Chemical Society Reviews, 8619-8635 (2015) (Year: 2015).*

* cited by examiner

*Primary Examiner* — Alexander R Pagano
(74) *Attorney, Agent, or Firm* — Novick, Kim & Lee, PLLC; Allen Xue

(57) ABSTRACT

Provided are a preparation method for a crystalline form of the compound represented by formula (A), as well as a method for preparation thereof, a composition thereof, and an application thereof in preparing an angiotensin II receptor antagonist or an application in preparing a drug for preventing and/or treating hypertension, chronic heart failure and diabetic nephropathy.

20 Claims, 9 Drawing Sheets

CRYSTALLINE FORM OF CHEMICAL COMPOUND, AND PREPARATION METHOD, COMPOSITION, AND APPLICATION THEREOF

TECHNICAL FIELD

Embodiments of the present disclosure relate to crystalline forms of a compound, a preparation method, a composition and applications thereof.

BACKGROUND

Hypertension is the most common cardiovascular disease and is also a major risk factor leading to increased morbidity and mortality of congestive heart failure, stroke, coronary heart disease, renal failure, and aortic aneurysms. Antihypertensive drugs play an important role in the treatment and prevention of hypertension. With the deepening of the understanding of the pathogenesis of hypertension, many antihypertensive drugs with better curative effects, such as diuretics, β-blockers, calcium channel antagonists, angiotensin converting enzyme inhibitors (ACEI,-pril), Angiotensin II AT1 receptor antagonist (ARB, sartan), has been continuously discovered and successfully applied in clinical practice. After years of clinical practice, it has been confirmed that the sartan of the AT1 receptor antagonist, due to its stable antihypertensive effect, good curative effect, long duration of action, good patient tolerance as well as many advantages especially in preventing stroke, delaying diabetes and non-diabetic nephropathy, improving left ventricular hypertrophy and protecting target organs, without affecting bradykinin degradation and prostaglandin synthesis so as not to cause dry cough and angioedema, has become the mainstream of the global antihypertensive drug market. However, the effective ratio of sartan antihypertensive drugs is only about 50-60%, and there exists a certain degree of adverse effect of sartans. Therefore, the development of a small-dose as well as long-acting antihypertensive drug with stronger antihypertensive effect, less adverse effect and better protection of target organs has become a hot research direction.

The Chinese Patent Application (Publication No. CN103709154A) discloses a compound of the formula (B) for the first time:

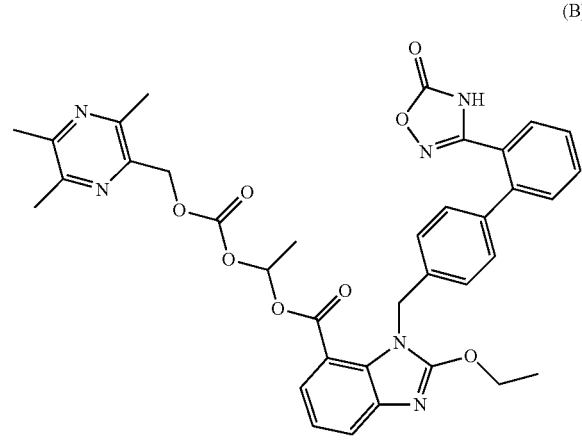

(B)

The above compound is a sartan drug which is coupled with ligustrazine and is a prodrug of angiotensin II receptor antagonist azisartan (TAK-536). The compound releases hydroxyprosin in vivo, which makes an effective synergistic action with azilsartan, accordingly enhancing its antihypertensive effect as well as contributing to reduction of heart rate and adverse effect, and further bringing desired protective effect on the heart and kidney of patients.

A potassium salt of compound (B), represented by the compound of formula (A) as below, has been discovered by the applicant in further studies, which has better solubility, higher bioavailability, more potent and longer-lasting antihypertensive effect, more obvious and sustainable effect of lowering heart rate, higher safety, as well as desired protective effect on the heart and kidney function of patients, and can be used for preventing and/or treating hypertension, chronic heart failure, diabetic nephropathy, and the like,

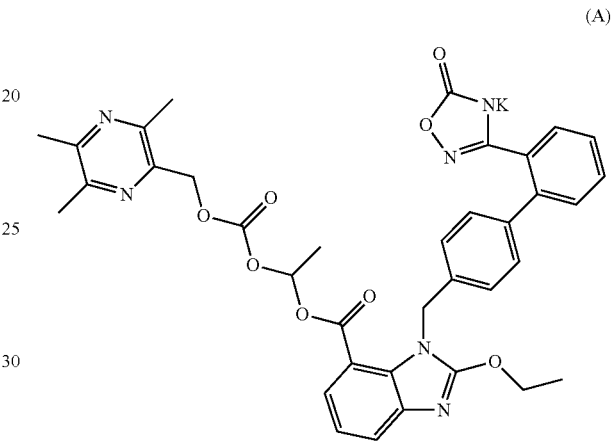

(A)

However, there is still demand for further development of a more suitable form of the above compounds.

SUMMARY

An embodiment of the present disclosure provides a crystalline form of a compound of formula (A):

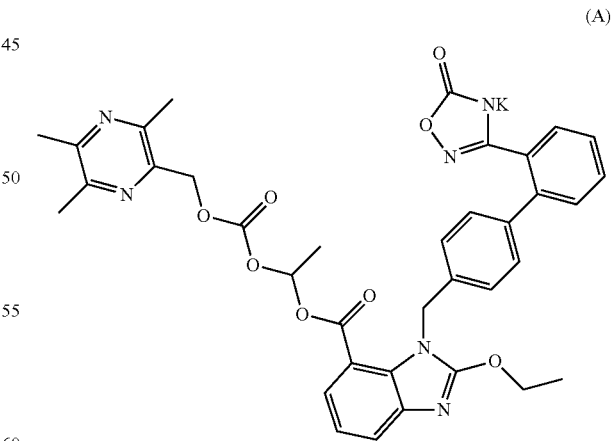

(A)

wherein, the crystalline form comprises one or more selected from the group consisting of: a crystalline form I, a crystalline form II, a crystalline form III and a crystalline form IV, wherein, a X-ray powder diffraction pattern of the crystalline form I comprises characteristic peaks at diffraction angles (2-Theta) of 5.3±0.2°, 8.6±0.2°; preferably, the X-ray powder diffraction pattern of the crystalline form I further comprises characteristic peaks at diffraction angles (2-Theta) of 13.3±0.2°, 20.1±0.2°; further preferably, the X-ray powder diffraction pattern of the crystalline form I further comprises characteristic peaks at diffraction angles (2-Theta) of 6.3±0.2°, 10.6±0.2°, 26.3±0.2°; more preferably, the X-ray powder diffraction pattern of the crystalline form I further comprises characteristic peaks at diffraction angles (2-Theta) of 12.7±0.2°; most preferably, the X-ray powder diffraction pattern of the crystalline form I comprises characteristic peaks at diffraction angles (2-Theta) substantially as shown in FIG. 1;

a X-ray powder diffraction pattern of the crystalline form II comprises characteristic peaks at diffraction angles (2-Theta) of 4.7±0.2°; preferably, the X-ray powder diffraction pattern of the crystalline form II further comprises characteristic peaks at diffraction angles (2-Theta) of 7.3±0.2°, 9.6±0.2°, 15.2±0.2°, 26.3±0.2°; further preferably, the X-ray powder diffraction pattern of the crystalline form II further comprises characteristic peaks at diffraction angles (2-Theta) of 11.8±0.2°, 24.6±0.2°; more preferably, the X-ray powder diffraction pattern of the crystalline form II further comprises characteristic peaks at diffraction angles (2-Theta) of 22.6±0.2°; most preferably, the X-ray powder diffraction pattern of the crystalline form II comprises characteristic peaks at diffraction angles (2-Theta) substantially as shown in FIG. 2;

a X-ray powder diffraction pattern of the crystalline form III comprises characteristic peaks at diffraction angles (2-Theta) of 5.2±0.2°, 8.0±0.2°; preferably, the X-ray powder diffraction pattern of the crystalline form III further comprises characteristic peaks at diffraction angles (2-Theta) of 12.4±0.2°, 13.6±0.2°; further preferably, the X-ray powder diffraction pattern of the crystalline form III further comprises characteristic peaks at diffraction angles (2-Theta) of 19.2±0.2°; more preferably, the X-ray powder diffraction pattern of the crystalline form III further comprises characteristic peaks at diffraction angles (2-Theta) of 10.3±0.2°, 12.2±0.2°, 21.4±0.2°; most preferably, the X-ray powder diffraction pattern of the crystalline form III comprises characteristic peaks at diffraction angles (2-Theta) substantially as shown in FIG. 3;

a X-ray powder diffraction pattern of the crystalline form IV comprises characteristic peaks at diffraction angles (2-Theta) of 7.4±0.2°, 14.7±0.2°, 16.0±0.2°; preferably, the X-ray powder diffraction pattern of the crystalline form IV further comprises characteristic peaks at diffraction angles (2-Theta) of 8.4±0.2°, 22.6±0.2°, 23.2±0.2°, 29.7±0.2°; more preferably, the X-ray powder diffraction pattern of the crystalline form IV further comprise characteristic peaks at diffraction angles (2-Theta) of 24.0±0.2°; most preferably, the X-ray powder diffraction pattern of the crystalline form IV comprise characteristic peaks at diffraction angles (2-Theta) substantially as shown in FIG. 4.

In an embodiment of the present disclosure, for example, a DSC spectrum of the crystalline form I shows a melting temperature at 184±5° C.; a DSC spectrum of the crystalline form II shows a melting temperature at 145±5° C.; a DSC spectrum of the crystalline form III shows a melting temperature at 187±5° C.; a DSC spectrum of the crystalline form IV shows a melting temperature at 145±5° C.

In an embodiment of the present disclosure, for example, a DSC spectrum of the crystalline form I shows a decomposition temperature at 180±5° C.; a DSC spectrum of the crystalline form II shows a decomposition temperature at 148±5° C.; a DSC spectrum of the crystalline form III shows a decomposition temperature at 183±5° C.; a DSC spectrum of the crystalline form IV shows a decomposition temperature at 149±5° C.

In an embodiment of the present disclosure, for example, the crystalline form I has an DSC-TGA substantially as shown in FIG. 10; the crystalline form II has an DSC-TGA substantially as shown in FIG. 11; the crystalline form III has an DSC-TGA substantially as shown in FIG. 12; the crystalline form IV has an DSC-TGA substantially as shown in FIG. 13.

An embodiment of the present disclosure provides a composition or a mixture, comprising one of the crystalline forms I, II, III, IV, or a mixture of two or more of the crystalline forms I, II, III, IV in any ratio.

In an embodiment of the present disclosure, for example, a composition or a mixture is provided, comprising the crystalline forms I and II in any ratio. In an embodiment of the present disclosure, for example, a mixture of the crystalline forms I and II in any ratio is provided.

Since mutual transformation between the crystalline form I and the crystalline form II may occur under some conditions, it will be understood by those skilled in the art that the ratio of the crystalline form I and the crystalline form II in their mixture is not particularly limited. In an embodiment of the present disclosure, for example, a weight ratio of the crystalline form I to the crystalline form II may be from 1:99 to 99:1, such as from 5:95 to 95:5. As an example, a weight ratio of the crystalline form I to the crystalline form II may be 1:9-9:1, 2:8-8:2, 3:7-7:3, 4:6-6:4 or 5:5.

An embodiment of the present disclosure provides methods for the preparation of the crystalline forms I, II, III and IV.

The compound of formula (B) can be prepared by methods known in the art, such as those disclosed in CN 103709154 A. CN 103709154 A is incorporated herein in its entirety. The compound of formula (A) can be prepared by reacting the compound of formula (B) with a potassium salt reagent.

An embodiment of the present disclosure provides a method of preparation of the crystalline form I. The method comprises stirring a suspension of the compound of formula (A), adding an anti-solvent to the solution of the compound of formula (A), cooling the solution of the compound of formula (A), placing the compound of formula (A) in a solvent atmosphere, or stirring a suspension of the crystalline form III and/or the crystalline form IV of the compound of formula (A). For example, one or more proceedings as described below may be selected:

(1) adding a solvent to the compound of formula (A) to obtain a suspension, and then stirring to obtain the crystalline form I; preferably, the solvent is one or more selected from a mixture of ethanol and isopropyl ether, a mixture of ethanol and n-heptane, a mixture of isopropanol and n-heptane, and a mixture of tetrahydrofuran and n-heptane; more preferably, the volume ratio of the two solvents in the mixture is from 1:8 to 8:1, and most preferably from 1:5 to 5:1; preferably, the suspension is stirred at room temperature for 0.5 to 3 days, most preferably, the suspension is stirred at room temperature for 1-2 days;

(2) dissolving the compound of formula (A) into a good solvent to obtain a clear solution, and adding an anti-solvent while stirring to obtain the crystalline form I; preferably, the good solvent is one or more selected from the group consisting of methanol, ethanol and n-butanol, and the anti-solvent is one or more selected from the group consisting of isopropyl ether, methyl tert-butyl ether and methylcyclohexane;

(3) dissolving the compound of formula (A) in a solvent under heating to obtain a clear solution, and cooling the solution to obtain the crystalline form I; preferably, the solvent is selected from a mixture of ethanol and isopropyl ether, a mixture of ethanol and ethyl acetate, a mixture of ethanol and methyl tert-butyl ether, a mixture of ethanol and n-heptane, a mixture of ethanol and methylcyclohexane, or a mixture of n-butanol and n-heptane; more preferably, the volume ratio of the two solvents in the mixture is from 1:8 to 8:1, and most preferably from 1:5 to 5:1; preferably, the heating temperature is from 40° C. to 90° C., and most preferably from 50° C. to 70° C.;

(4) placing the compound of formula (A) in a solvent atmosphere of ethanol for 1-3 days to obtain the crystalline form I; and (5) adding the crystalline form III and/or the crystalline form IV of the compound of formula (A) into a solvent to form a suspension, stirring and drying to obtain the crystalline form I; preferably, the solvent is selected from an ester solvent such as ethyl acetate, isopropyl acetate or a mixture thereof.

An embodiment of the present disclosure provides a method of preparation of the crystalline form II. The method comprises evaporating a solution of the compound of formula (A) to dryness, stirring a solution, a saturated solution, a supersaturated solution or a suspension of the compound of formula (A), adding an anti-solvent to the solution of the compound of formula (A), cooling the solution of the compound of formula (A), and placing the compound of formula (A) in a solvent atmosphere. For example, one or more proceedings as described below may be selected:

(1) dissolving the compound of formula (A) in a solvent to obtain a clear solution, evaporating the solution to dryness at room temperature to give the crystalline form II; preferably, the solvent is selected from a mixture of ethanol and ethyl acetate, a mixture of acetone and ethyl acetate, a mixture of acetone and isopropyl ether, or a mixture of acetone and n-heptane; more preferably, the volume ratio of the two solvents in the mixture is from 1:8 to 8:1, and most preferably from 1:5 to 5:1;

(2) adding the compound of formula (A) to a solvent to obtain a clear solution, a saturated solution, a supersaturated solution or a suspension, and stirring to obtain the crystalline form II; preferably, the solvent is selected from isopropanol, sec-butanol, ethyl acetate, toluene, isopropyl acetate, a mixture of ethanol and ethyl acetate, a mixture of ethanol and isopropyl acetate, a mixture of ethanol and toluene, a mixture of acetone and n-heptane, or a mixture of 1,4-dioxane and n-heptane; more preferably, the volume ratio of the two solvents in the mixture is from 1:8 to 8:1, and most preferably from 1:5 to 5:1; preferably, stirring at room temperature for 10 minutes to 5 days, most preferably stirring at room temperature for 3 hours to 3 days;

(3) dissolving the compound of formula (A) in a good solvent to obtain a clear solution, and adding an anti-solvent under stirring to obtain the crystalline form II; preferably, the good solvent is selected from methyl ethyl ketone, dimethyl sulfoxide or 1,4-dioxane, and the anti-solvent is selected from n-heptane, isopropyl ether or isopropyl acetate;

(4) dissolving the compound of formula (A) in a solvent under heating to obtain a clear solution, and cooling the solution to obtain the crystalline form II; preferably, the solvent is selected from sec-butanol, nitromethane, acetone, or tetrahydrofuran; preferably, the heating temperature is from 40° C. to 90° C., and most preferably, the heating temperature is from 50° C. to 70° C.;

(5) placing a saturated ethanol solution of the compound of the formula (A) in a solvent atmosphere of isopropyl ether or isopropyl acetate until the crystalline form II is precipitated out; and (6) placing the compound of formula (A) in a solvent atmosphere of toluene, isopropanol, tetrahydrofuran or ethyl acetate for 1-3 days to obtain the crystalline form II.

An embodiment of the present disclosure provides a method of preparation of crystalline form III. The method comprises stirring a suspension of the compound of formula (A), or placing the compound of formula (A) in a solvent atmosphere. For example, one or more proceedings as described below may be selected:

(1) adding tetrahydrofuran to the compound of the formula (A) to obtain a suspension and stirring the suspension to obtain the crystalline form III; preferably, stirring the suspension at room temperature for 12 hours to 5 days, and most preferably, stirring the suspension at room temperature for 1-3 days; and (2) placing a tetrahydrofuran saturated solution of the compound of formula (A) in a solvent atmosphere of isopropyl ether until the crystalline form III is precipitated.

An embodiment of the present disclosure provides a method of preparation of the crystalline form IV. The method comprises adding an anti-solvent to the solution of the compound of formula (A). For example, the method comprises dissolving the compound of formula (A) in n-butanol to give a clear solution, and adding n-heptane under stirring to obtain the crystalline form IV.

An embodiment of the present disclosure provides a method of preparation of a mixture (or a mixed crystal) of the crystalline form I and the crystalline form II. The method comprises stirring a suspension of the crystalline form II at room temperature or at elevated temperature to crystallize. For example, one or more proceedings as described below may be selected:

(1) adding isopropyl acetate to the crystalline form II to obtain a suspension, and stirring at 50° C. to 90° C. to obtain a mixture of the crystalline form I and the crystalline form II; preferably, stirring the suspension at 50° C. to 90° C. for 3 hours to 3 days, and most preferably stirring the suspension at 60° C. to 90° C. for 5 hours to 1 day;

(2) pulverizing and sieving a wet product of the crystalline form II followed by vacuum drying at 40° C. to 60° C. (such as 50° C.), preferably for 3 hours to 3 days, for example 24 h;

(3) vacuum drying a wet product of the crystalline form II at 40° C. to 60° C. (such as 50° C.) for 3 hours to 3 days followed by micronizing; and (4) adding a solvent to the crystalline form II to obtain a suspension, stirring the suspension at room temperature to obtain a mixture of the crystalline form I and the crystalline form II; preferably, the solvent is selected from methyl tert-butyl ether or a mixture of ethanol and methylcyclohexane; more preferably, the volume ratio of the two solvents in the mixture is from 1:8 to 8:1, and most preferably from 1:6 to 5:1; preferably, stirring for 3 hours to 3 days, and most preferably, stirring for 1-3 days.

In an embodiment of the present disclosure, for example, the crystalline form I of embodiments of the present invention can also be used as a starting material for the preparation of the crystalline form II; for example, the crystalline form I is added into an ester solvent such as ethyl acetate, isopropyl acetate or a mixture thereof to form a suspension, followed by stirring at room temperature overnight to obtain the crystalline form II.

In an embodiment of the present disclosure, for example, the crystalline form III of embodiments of the present invention can also be used as a starting material for the preparation of the crystalline form II; for example, the crystalline form III is added to an ester solvent such as ethyl acetate, isopropyl acetate or a mixture thereof to form a suspension, followed by stirring at room temperature overnight to obtain the crystalline form II.

In an embodiment of the present disclosure, for example, the crystalline form III of embodiments of the present invention can also be used as a starting material for the preparation of the crystalline form I; for example, the crystalline form III is added to an ester solvent such as ethyl acetate, isopropyl acetate or a mixture thereof to form a suspension, followed by stirring at room temperature overnight to obtain the crystalline form I.

In an embodiment of the present disclosure, for example, the crystalline form IV of embodiments of the present invention can also be used as a starting material for the preparation of the crystalline form I; for example, the crystalline form IV is dried overnight at room temperature to obtain the crystalline form I.

An embodiment of the present disclosure provides a pharmaceutical composition comprising a therapeutically effective amount of any one of the crystalline forms I, II, III, IV of embodiments of the present invention, or a mixture of two or more thereof in any ratio and a pharmaceutically acceptable carrier. For example, the pharmaceutical composition comprises a therapeutically effective amount of one of crystalline forms I, II of embodiments of the present invention, or a mixture thereof in any ratio and a pharmaceutically acceptable carrier. For example, the weight ratio of the crystalline form I to the crystalline form II is from 1:99 to 99:1. The pharmaceutical composition of embodiments of the present invention can be formulated into powders, tablets (including various coated tablets, sustained release or controlled release tablets), troches, capsules (including soft capsules and hard capsules), granules, pills, dispersible powders, aqueous or oily suspensions, aqueous or oily solutions, emulsions, elixirs, syrups and the like, all of which are suitable for oral administration; powders or liquid aerosols suitable for inhalation; creams, ointment, gel, aqueous or oily solution, aqueous or oily suspension and the like, which are suitable for topical use; sterile aqueous or oily injection, dry powder injections, suppositories, and the like, which are suitable for parenteral administration such as intravenous, subcutaneous or intramuscular injection. Pharmaceutically acceptable carriers include, but are not limited to, excipients, lubricants, binders, disintegrants, water soluble polymers, inorganic salts, solvents, dissolution aids, suspending agents, isotonic agents, buffers, preservatives, antioxidants, colorants, sweeteners, sour agents, foaming agents, flavoring agents, and the like.

The pharmaceutical composition of embodiments of the present invention may further comprise other active ingredients, such as other active ingredients for preventing and/or treating hypertension, like calcium ion antagonists (dihydropyridines, arylalkylamines, phenylthiazides and triphenyl piperazines).

Suitable amounts of any one of the crystalline forms I, II, III, IV or a mixture of two or more thereof in any ratio, as well as various pharmaceutically acceptable carriers and/or other active ingredients in the pharmaceutical composition, can be determined by a person skilled in the art, according to conventional methods. The term "effective amount" or "therapeutically effective amount" refers to the amount, sufficient to achieve desired application (including but not limited to disease treatment as defined below), of any one of the crystalline forms I, II, III, IV of embodiments of the present invention or a mixture of two or more thereof in any ratio. The therapeutically effective amount may vary depending on the desired application (in vitro or in vivo), or the subject and disease condition being treated, such as the weight and age of the subject, the severity of the disease condition, and the mode of administration, etc, which is readily determined by the ordinary skilled person in the art. The particular dosage will vary depending on the particular compound selected, the dosage regimen based, whether it is administered in combination with other compounds, the timing of administration, the tissue to be administered, and the physical delivery system to carry it.

An embodiment of the present disclosure provides a use of any one of the crystalline forms I, II, III, IV or a mixture of two or more thereof in any ratio, or the pharmaceutical composition for preparing an angiotensin II receptor antagonist or a medicament for the prevention and/or treatment of hypertension, chronic heart failure, diabetic nephropathy.

An embodiment of the present disclosure provides a use of any one of the crystalline forms I, II, III, IV or a mixture of two or more thereof in any ratio, or the pharmaceutical composition as an angiotensin II receptor antagonist or for the prevention and/or treatment of hypertension, chronic heart failure, diabetic nephropathy.

It has been found by the inventors that the crystalline forms I, II and III described in this specification have stable chemical properties, with less impurities generated after placed for certain time, relative to the amorphous form. Moreover, the crystal stability of the crystalline forms I, II, and III is superior to the crystalline form IV at room temperature. Further, the crystalline forms of embodiments of the present invention are relatively stable under tabletting conditions or under high temperature or high humidity conditions with respect to the amorphous form. These characteristics make the crystalline forms of embodiments of the present invention more favorable to the quality control of drugs and druggability properties. Further, the bioavailability of the crystalline forms I, II, III such as the mixture of the crystalline forms I and II is also improved relative to the amorphous form.

Moreover, it has also been found that the crystalline form I of embodiments of the present invention can be used as a starting material for preparing the crystalline form II, the crystalline form III can be used as a starting material for preparing the crystalline form II, the crystalline form III can be used as a starting material for preparing the crystalline form I, and the crystalline form IV can be used as a starting material for the preparation of the crystalline form I. Thus, more options for the preparation of the crystalline forms of the compound of formula (A) are provided in embodiments of the present invention, which allows for the highly selective acquisition of the target crystalline forms under milder conditions.

The term "crystal" means crystal structures in which a compound can crystallize in different crystal packing arrangements of its molecular and/or ion, all of which have the same elemental composition.

The term "amorphous form" refers to a noncrystalline solid state form of a molecular and/or an ion, which does not show a defined X-ray powder diffraction pattern with a clear maximum.

The term "X-ray powder diffraction pattern substantially as shown in figure" or "having characteristic peaks at diffraction angles (2-Theta) substantially as shown in Figure in a X-ray powder diffraction pattern" means at least 50%, or at least 60%, or at least 70%, or at least 80%, or at least 90%, or at least 95%, or at least 99% of the main characteristic peaks shown in the X-ray powder diffraction pattern appear in the X-ray powder diffraction pattern; wherein the main characteristic peaks refer to those with relative intensity greater than 10%, and preferably greater than 30%, using the highest peak as the reference (the relative intensity of the highest peak is specified as 100%).

BRIEF DESCRIPTION OF THE DRAWINGS

In order to clearly illustrate the technical solution of the embodiments of the disclosure, the drawings of the embodiments will be briefly described in the following, it is obvious that the described drawings are only related to some embodiments of the disclosure and thus are not limitative of the disclosure.

DETAILED DESCRIPTION

In order to make objects, technical details and advantages of the embodiments of the disclosure apparent, the technical solutions of the embodiment will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Example 1: Preparation of a Compound of Formula (A)

A compound of the formula (B) (1.0 g) was dissolved in dichloromethane (5 ml), and the mixture was stirred at room temperature to form a solution, which was then added with potassium phthalimide (0.27 g), kept for 4 hours at room temperature, and cooled to −50° C., followed by filtration and drying via rotary evaporation to obtain the compound of formula (A) (amorphous form).

Melting point: 135-145° C. MS/HRMS m/z: 717 [M+H]$^+$; 677 [M-K]$^-$. $^1$H-NMR (400 MHz, DMSO-d$_6$) δ: 1.44 (t, 3H), 1.46 (t, 3H), 2.38 (s, 3H), 2.41 (s, 3H), 2.44 (s, 3H), 4.64 (q, 2H), 5.29 (d, 1H), 5.32 (d, 1H), 5.52 (d, 1H), 5.56 (d, 1H), 6.86 (q, 1H), 6.90 (d, 2H), 7.18 (m, 2H), 7.22 (d, 2H), 7.33 (m, 1H), 7.36 (m, 1H), 7.46 (d, 1H), 7.52 (dd, 1H), 7.75 (d, 1H).

Figure 5:
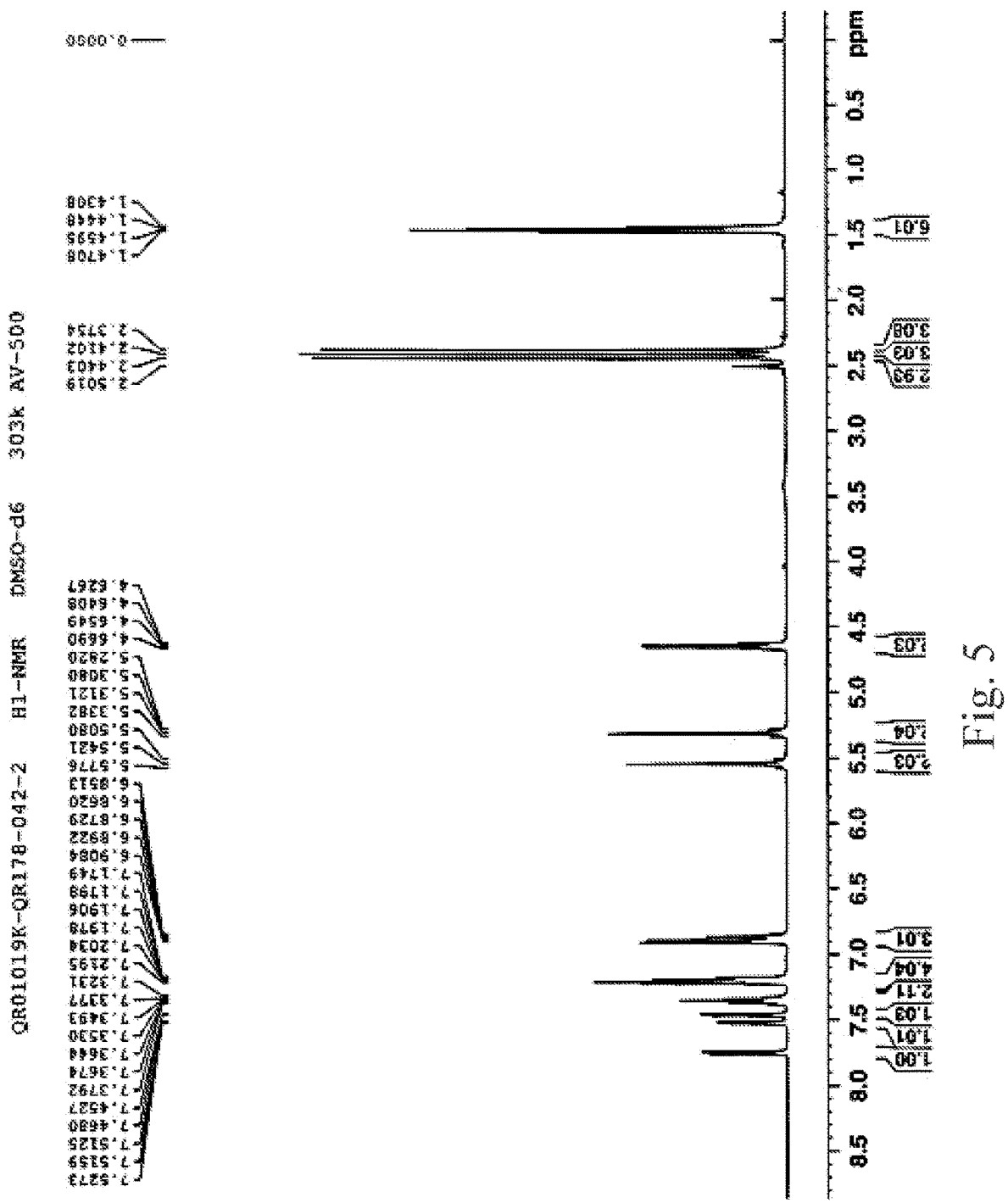
FIG. 5 is a $^1$H-NMR spectrum of the compound of formula (A)
Figure 6:
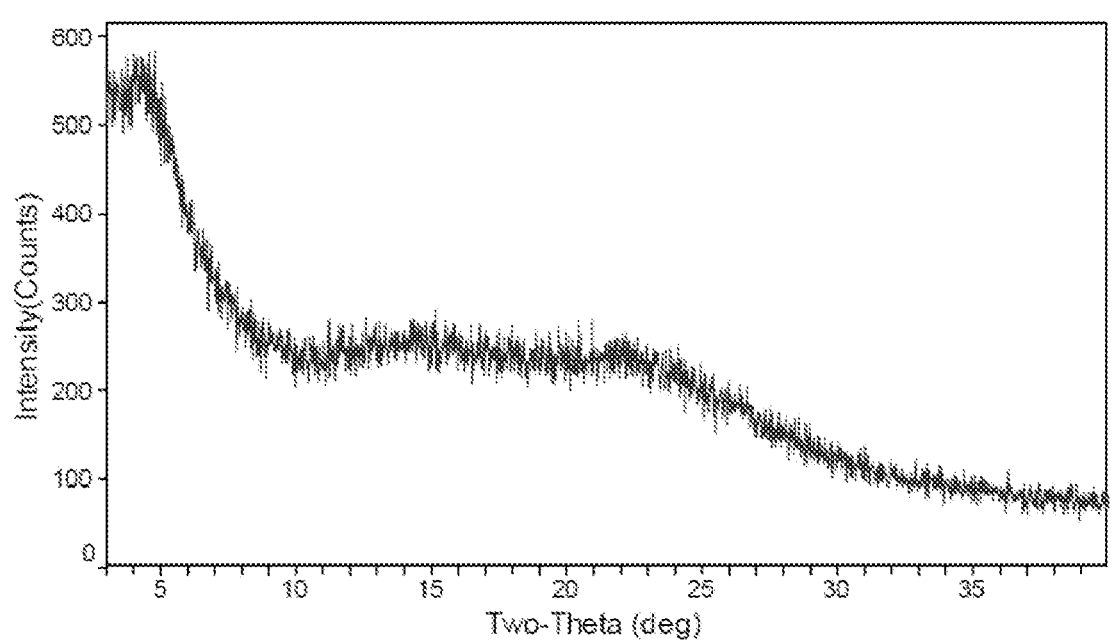
FIG. 6 is an X-ray powder diffraction pattern of the amorphous form of the compound of formula (A)

The $^1$H-NMR spectrum and the X-ray powder diffraction pattern are respectively shown in FIG. 5 and FIG. 6.

Example 2: Antihypertensive Efficacy Test of the Compound of Formula (A) in Spontaneously Hypertensive Rats 12-week-old spontaneously hypertensive rats (hereinafter referred to as SHR, purchased from Beijing Weitong Lihua Experimental Animal Technology Co., Ltd.) were anesthetized with 2.5% sodium pentobarbital for intraperitoneal injection. After that, the blood pressure sensing catheter of hypertension implant was inserted into their abdominal aorta, while the implant was fixed to the abdominal wall, and then postoperative daily care was performed after suturing.

Rats with systolic blood pressure exceeding 160 mm Hg were divided into 3 groups (control group, compound (A) group and compound (B) group), wherein each group has 8 rats. The control group was administrated 0.5% sodium carboxymethyl cellulose (hereinafter referred to as CMC-Na); the compound (B) group and the compound (A) group were respectively administered the compound (B) and the compound (A), both of which were dissolved by 0.5% CMC-Na, by intragastric administration, at a dose of 1 mg/kg (calculated by the effective dose of valsartan) and a volume calculated by 4 mL/kg.

The systolic blood pressure and heart rate of SHR were compared before and after administration (the systolic blood pressure and heart rate of SHR before administration as reference value), which were detected three times at each time point with the average value recorded. The results are shown in Tables 1 and 2 below.

TABLE 1

Systolic blood pressure change at each time point before and after intragastric administration of the compound of formula (B) and compound of formula (A) (average (mmHg) ± standard error)

| Group | Before administration | 1 hour after administration | 3 hours after administration | 5 hours after administration |
|---|---|---|---|---|
| Control group | 0.0 ± 0.0 | 5.4 ± 7.1 | −3.5 ± 4.6 | 4.5 ± 4.0 |
| Compound (B) group | 0.0 ± 0.0 | −4.9 ± 4.8 | −22.0 ± 3.6* | −30.5 ± 3.5* |

TABLE 1-continued

Systolic blood pressure change at each time point before and after intragastric administration of the compound of formula (B) and compound of formula (A) (average (mmHg) ± standard error)

| Compound (A) group | 0.0 ± 0.0 | −7.0 ± 3.4 | −34.3 ± 1.9* | −46.5 ± 2.5* |
|---|---|---|---|---|

| Group | 7 hours after administration | 10 hours after administration | 24 hours after administration |
|---|---|---|---|
| Control group | 4.1 ± 3.2 | −2.9 ± 2.3 | −2.7 ± 6.4 |
| Compound (B) group | −38.8 ± 2.3* | −33.0 ± 1.7* | −10.2 ± 2.1 |
| Compound (A) group | −49.4 ± 4.1* | −45.3 ± 3.3* | −25.9 ± 3.4* |

*$P < 0.01$ (relative to the control group).

It can be seen from the results in Table 1 that after 3 hours of administration, the systolic blood pressure of the compound (B) group or the compound (A) group is significantly decreased compared with the control group, and the drug efficacy characteristic peaks 5-7 hours after administration, and the compound (A) group is more potent with longer-lasting antihypertensive effect, compared with the compound (B) group.

TABLE 2

Heart rate change before and after oral administration of the compound of formula (B) and compound of formula (A) (average (times/minute) ± standard error)

| Group | Before administration | 1 hour after administration | 3 hours after administration | 5 hours after administration |
|---|---|---|---|---|
| Control group | 0.0 ± 0.0 | 0.14 ± 2.9 | 6.4 ± 2.8 | −0.3 ± 2.7 |
| Compound (B) group | 0.0 ± 0.0 | −3.4 ± 2.6 | −2.33 ± 2.6* | −6.5 ± 2.8* |
| Compound (A) group | 0.0 ± 0.0 | −3.6 ± 2.4 | −5.0 ± 2.5* | −10.1 ± 3.0* |

| Group | 7 hours after administration | 10 hours after administration | 24 hours after administration |
|---|---|---|---|
| Control group | −0.1 ± 2.9 | −2.5 ± 2.5 | 4.3 ± 2.8 |
| Compound (B) group | −6.2 ± 3.0* | −12.3 ± 2.8* | −6.7 ± 2.6* |
| Compound (A) group | −17.5 ± 3.0* | −25.4 ± 2.4* | −28.6 ± 8* |

*$P < 0.05$ (relative to the one-way ANOVA of the control group).

It can be seen from the results in Table 2 that the compound (A) group has more potent with longer-lasting effect of lowering heart rate compared with the compound (B) group.

Example 3: Preparation of Crystalline Form I of the Compound (A)

Figure 1:
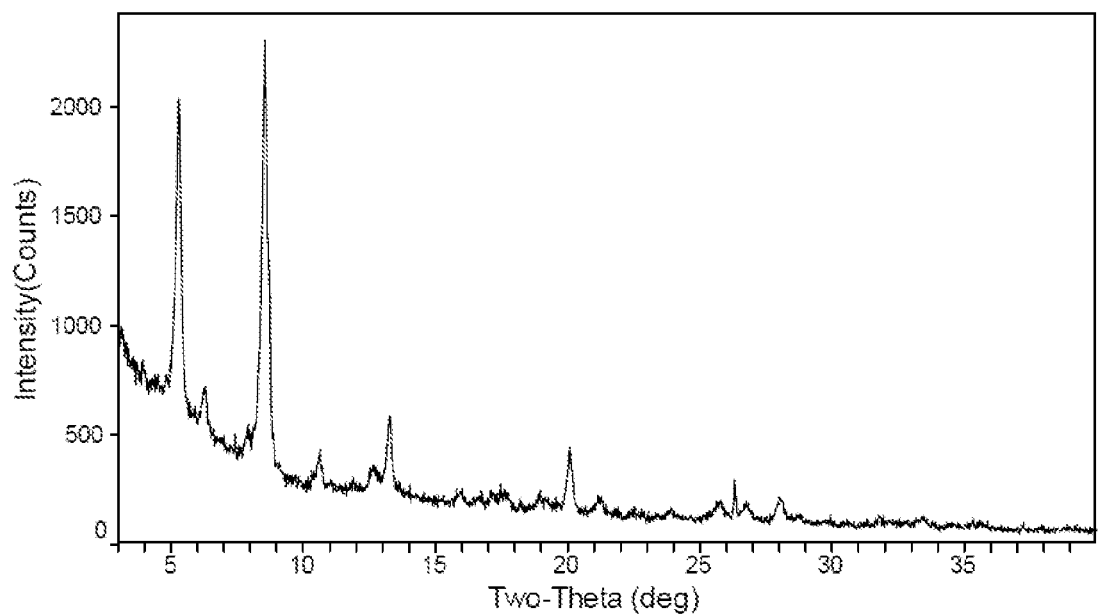
FIG. 1 is an X-ray powder diffraction pattern of the crystalline form I.

(1) 15 mg compound of formula (A) was added with a mixed solution of 0.2 ml of ethanol/isopropyl ether (1:5 v/v) to obtain a suspension, which was stirred at room temperature for 1 day, filtered, and dried to give a crystalline form I. The XRD detection pattern is shown in FIG. 1; DSC: 184° C. The crystalline form I was also prepared through the above procedures with the mixed solution replaced by ethanol/n-heptane (1:5 v/v), isopropanol/n-heptane (1:5 v/v), or tetrahydrofuran/n-heptane (1:5 v/v).

(2) 15 mg compound of formula (A) was dissolved in 0.1 ml of methanol (good solvent) to obtain a clear solution, which was added with 1.0 ml of isopropyl ether (anti-solvent) while stirring to precipitate a solid, and then stirred, filtered and dried to give a crystalline form I. The crystalline form I was also prepared through the above procedures with the solvent replaced by ethanol (good solvent)/isopropyl ether (anti-solvent), ethanol (good solvent)/methyl tert-butyl ether (anti-solvent), ethanol (good solvent)/methylcyclohexane (anti-solvent), n-butanol (good solvent)/isopropyl ether (anti-solvent).

(3) 10 mg compound of formula (A) was dissolved in a mixed solution of ethanol/isopropyl ether (0.2 ml: 0.5 ml) at 60° C. to obtain a clear solution, which was cooled to give a crystalline form I. The crystalline form I was also prepared through the above procedures with the mixed solution replaced by ethanol/ethyl acetate (0.1 ml: 0.5 ml), ethanol/methyl tert-butyl ether (0.2 ml: 0.5 ml), ethanol/n-heptane (0.2 ml: 0.5 ml), ethanol/methylcyclohexane (0.2 ml: 0.5 ml), or n-butanol/n-heptane (0.2 ml: 0.5 ml).

(4) 8 mg compound of formula (A) was placed in a solvent atmosphere of ethanol (that is, placed in a large vessel containing ethanol) for 1 day, and dried to obtain a crystalline form I.

(5) 15 mg crystalline form III of the compound of formula (A) was added to 0.2 ml of ethyl acetate to form a suspension, stirred overnight, and dried to give a crystalline form I.

(6) 15 mg crystalline form IV of the compound of formula (A) was added to 0.2 ml of ethyl acetate to form a suspension, stirred overnight, and dried at room temperature to obtain a crystalline form I.

Example 4: Preparation of Crystalline Form II of the Compound (A)

Figure 2:
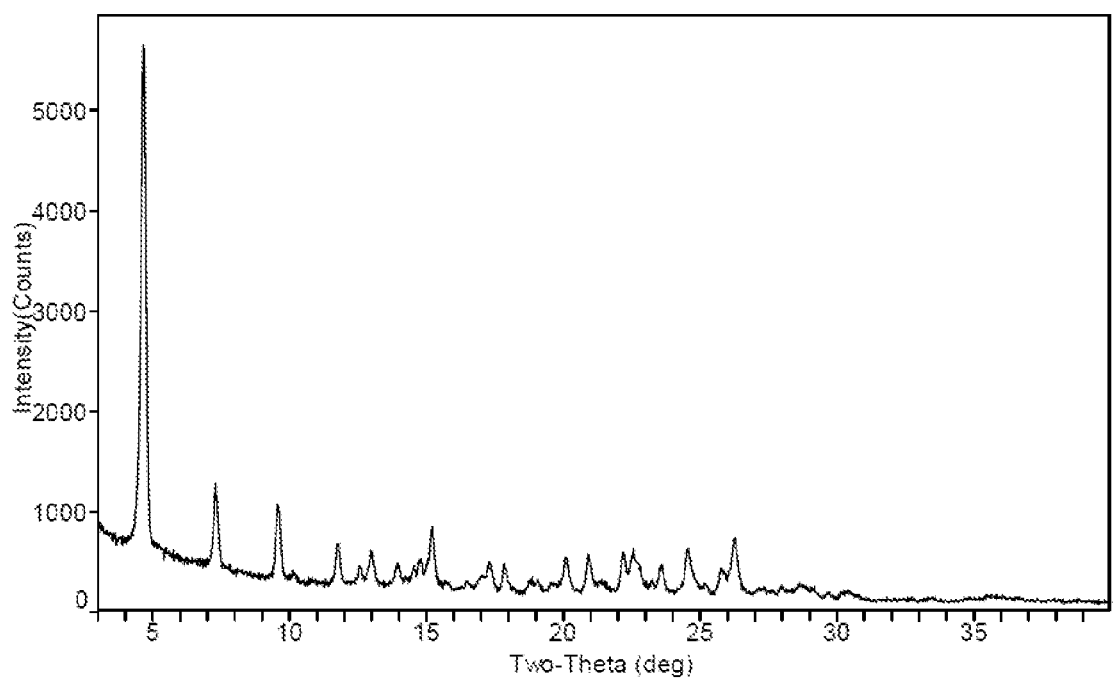
FIG. 2 is an X-ray powder diffraction pattern of the crystalline form II.

(1) 1.1 g compound of formula (A) was added with 10 ml of ethyl acetate to obtain a clear solution, which was stirred at room temperature for 3 hours, filtered and dried to obtain 0.88 g product. The XRD detection spectrum of the obtained crystalline form II is shown in FIG. 2; DSC: 145.4° C. It was found that with gradually reduced ethyl acetate, the crystalline form II can be obtained through stirring of a saturated solution, a supersaturated solution or a suspension of the compound of formula (A).

The crystalline form II was also prepared through the above procedures with the solvent (ethyl acetate) replaced by isopropanol, sec-butanol, isopropyl acetate, toluene, ethanol/ethyl acetate (1:5 v/v) mixed solution, ethanol/isopropyl acetate (1:5 v/v) mixed solution, ethanol/toluene (1:5 v/v) mixed solution, acetone/n-heptane (1:5 v/v) mixed solution, or 1,4-dioxane/n-heptane (1:5 v/v) mixed solution.

(2) 5 mg compound of formula (A) was dissolved in a mixed solution of ethanol/ethyl acetate (0.2 ml: 0.5 ml) to obtain a clear solution, which was evaporated to dryness at room temperature to obtain a crystalline form II. The crystalline form II was also prepared through the above procedures with the mixed solution replaced by acetone/ethyl acetate (1.0 ml: 0.5 ml), acetone/isopropyl ether (2.0 ml: 0.5 ml), or acetone/n-heptane (2.0 ml: 0.5 ml).

(3) 15 mg compound of formula (A) was dissolved in 0.8 ml butanone (good solvent) to obtain a clear solution, and added with 4.0 ml n-heptane (anti-solvent) under stirring to precipitate a solid, which was filtered and dried to give a crystalline form II. The crystalline form II was also prepared through the above procedures with the solvent replaced by methyl ethyl ketone (good solvent)/isopropyl ether (anti-solvent), dimethyl sulfoxide (good solvent)/isopropyl acetate (anti-solvent), or 1,4-dioxane (good solvent)/isopropyl ether (anti-solvent).

(4) 10 mg compound of formula (A) was dissolved in sec-butanol at 60° C. to obtain a clear solution, which was cooled to give a crystalline form II. The crystalline form II was also prepared through the above procedures with the solvent replaced by nitromethane, acetone or tetrahydrofuran.

(5) 5 mg compound of formula (A) was dissolved in an appropriate amount of ethanol to obtain a saturated solution, which was placed in a solvent atmosphere of isopropyl ether (that is, placed in a large vessel containing isopropyl ether) until precipitating a solid and then filtered and dried to obtain a crystalline form II. The crystalline form II was also obtained through the above procedures by replacing ethanol with isopropyl acetate.

(6) 8 mg compound of formula (A) was placed in a solvent atmosphere of toluene (that is, placed in a large vessel containing toluene) for 3 days, and dried to obtain a crystalline form II. The crystalline form II was also obtained through the above procedures by replacing toluene with isopropanol, tetrahydrofuran or ethyl acetate.

Example 5: Preparation of Crystalline Form III of Compound (A)

Figure 3:
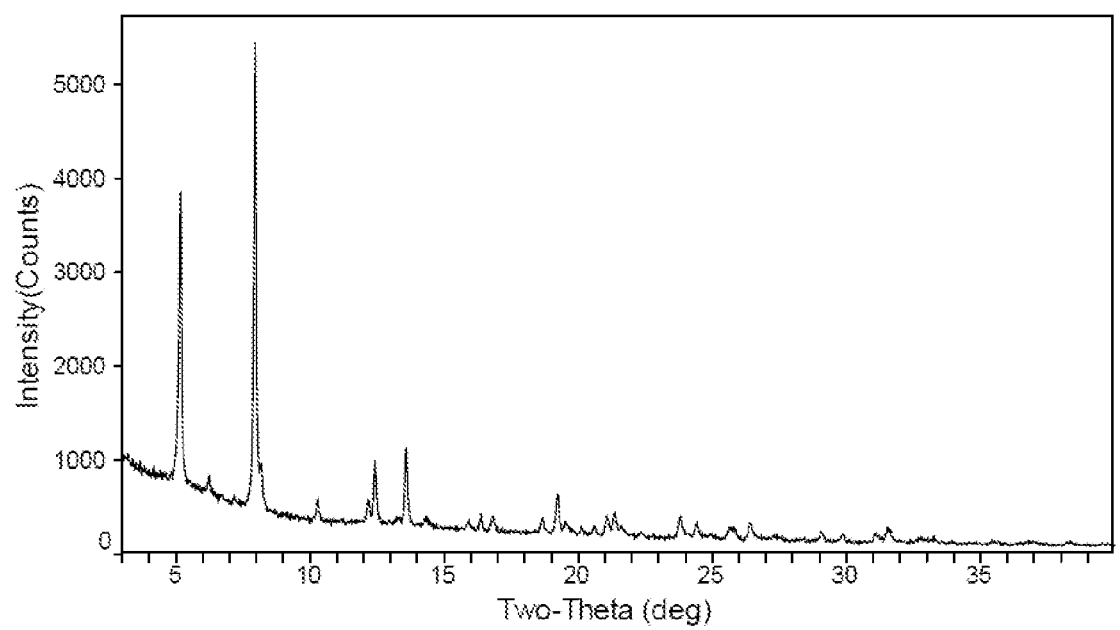
FIG. 3 is an X-ray powder diffraction pattern of the crystalline form III.

(1) 100 mg compound of formula (A) was added with 1.0 ml of tetrahydrofuran to obtain a suspension, which was stirred at room temperature for 1 day, filtered, and dried. The XRD detection spectrum of the obtained crystalline form III is shown in FIG. 3; DSC: 187.3° C.

(2) 5 mg compound of formula (A) was dissolved in an appropriate amount of tetrahydrofuran to obtain a saturated solution, which was placed in a solvent atmosphere of isopropyl ether (that is, placed in a large vessel containing isopropyl ether) to stand until precipitating a solid, and then filtered and dried to obtain a crystalline form III.

Example 6: Preparation of Crystalline Form IV of Compound (A)

Figure 4:
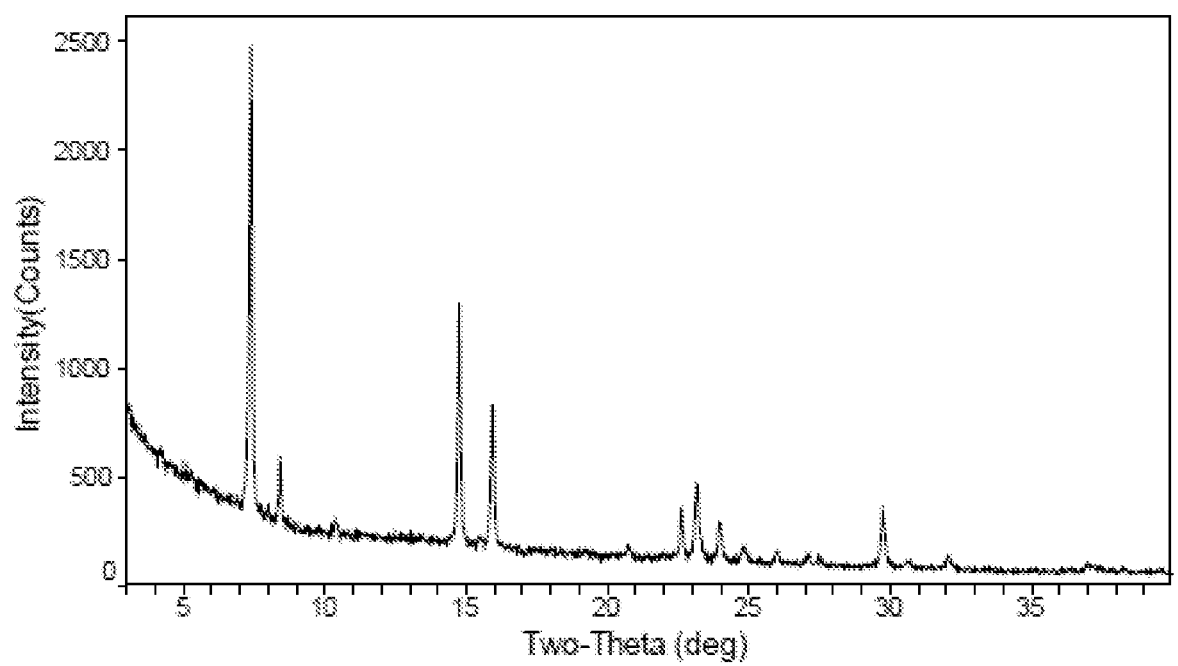
FIG. 4 is an X-ray powder diffraction pattern of the crystalline form IV.

50 mg compound of formula (A) was dissolved in 1.0 ml of n-butanol to obtain a clear solution, added with 5.0 ml n-heptane under stirring to precipitate a solid and filtered. The XRD spectrum of the obtained crystalline form IV is shown in FIG. 4; DSC melting point: 144.7° C.

Figure 7:
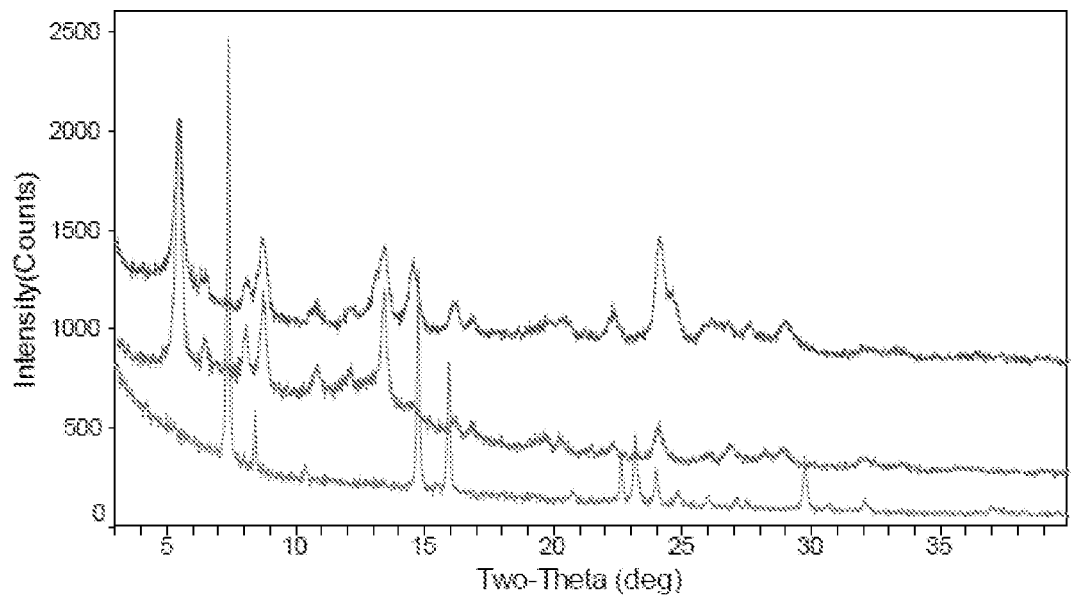
FIG. 7 is an X-ray powder diffraction pattern of the crystalline form IV before and after drying at room temperature (from top to bottom: the crystalline form I, the crystalline form IV after drying at room temperature and the crystalline form IV)

The crystalline form IV can be converted to crystalline form I by drying at room temperature, as shown in FIG. 7.

Example 7: Preparation of a Mixture of the Crystalline Form I and the Crystalline Form II (1) 100 mg of the crystalline form II was added with 2.5 ml isopropyl acetate to obtain a suspension, which was stirred in a water bath at 80° C. for 8 hours, filtered, and dried. It is determined by X-ray detection that the crude product contains about 95% of crystalline form I and about 5% of crystalline form II.

(2) 100 mg wet product of crystalline form II was pulverized, sieved, and vacuum-dried at 50° C. for 24 h. It is determined by X-ray detection that the crude product contains about 10% of crystalline form I and about 90% of crystalline form II.

(3) 100 mg wet product of crystalline form II was vacuum-dried at 50° C. for 24 h followed by micronization using a micro-powder machine. It is determined by X-ray detection that the crude product contains about 30% of crystalline form I and about 70% of crystalline form II.

(4) 15 mg crystalline form II was added with 0.5 ml methyl tert-butyl ether to obtain a suspension, which was stirred at room temperature for 3 days, filtered, and dried to obtain a mixture of crystalline form I and crystalline form II. A mixture of crystalline form I and crystalline form II is also obtained through the above procedures by replacing methyl tert-butyl ether with a mixed solution of ethanol/methyl cyclohexane (1:5 v/v).

Example 8: Competition Test at Room Temperature (1) Competition Experiment Between Crystalline Form I and Crystalline Form II Equivalent amounts of crystalline form I and crystalline form II samples were mixed well, added with 0.8 ml ethyl acetate to form a suspension, stirred overnight and detected by XRD. It is determined that the obtained product contains about 5% of the crystalline form I by comparing the XRD of the obtained product with an XRD of a mixture of crystalline form I and crystalline form II in which a ratio of the crystalline form I:the crystalline form II is gradually and equally increased. In terms of the significant weakening tendency of the characteristic peaks of crystalline form I, it can be expected that the crystalline form I will be completely transformed into the crystalline form II when given sufficient time. Consequently, it turns out that the stability of crystalline form II is better than that of form I under room temperature.

(2) Competition Experiment Between Crystalline Form II and Crystalline Form III

Equivalent amounts of crystalline form II and form III samples were mixed well, added with 0.2 ml ethyl acetate to form a suspension, which was stirred overnight to obtain a crystalline form II determined by XRD detection. It turns out that the crystalline form III in the mixture is completely transformed into the crystalline form II. Consequently, the stability of crystalline form II is better than that of form III under room temperature.

(3) Competition Experiment Between Crystalline Form I and Crystalline Form III

Equivalent amounts of crystalline form I and form III samples were mixed uniformly, added with 0.2 ml ethyl acetate to form a suspension, which was stirred overnight, to obtain a crystalline form I determined by XRD detection. It turns out that the crystalline form III in the mixture is completely transformed into the crystalline form I. Consequently, the stability of crystalline form I is better than that of the crystalline form III under room temperature.

(4) Comparative Experiment of Stability Between Crystalline Form III and Crystalline Form IV The crystalline form III and the crystalline form IV samples were respectively dried overnight at room temperature. It turns out by XRD detection that only no more than 30% of the crystalline form III was converted to the crystalline form I. However, the crystalline form IV is completely transformed into the crystalline form I, showing poor stability. It is revealed by the above results that the stability of the crystalline forms I, II and III is superior to that of the crystalline form IV at room temperature.

Example 9: Investigation of the Effects of Tabletting Processes on the Crystalline Form II Tabletting method: 50 mg of the crystalline form II was tableted under 20 kg and 25 kg pressure by a single punching machine.

Figure 8:
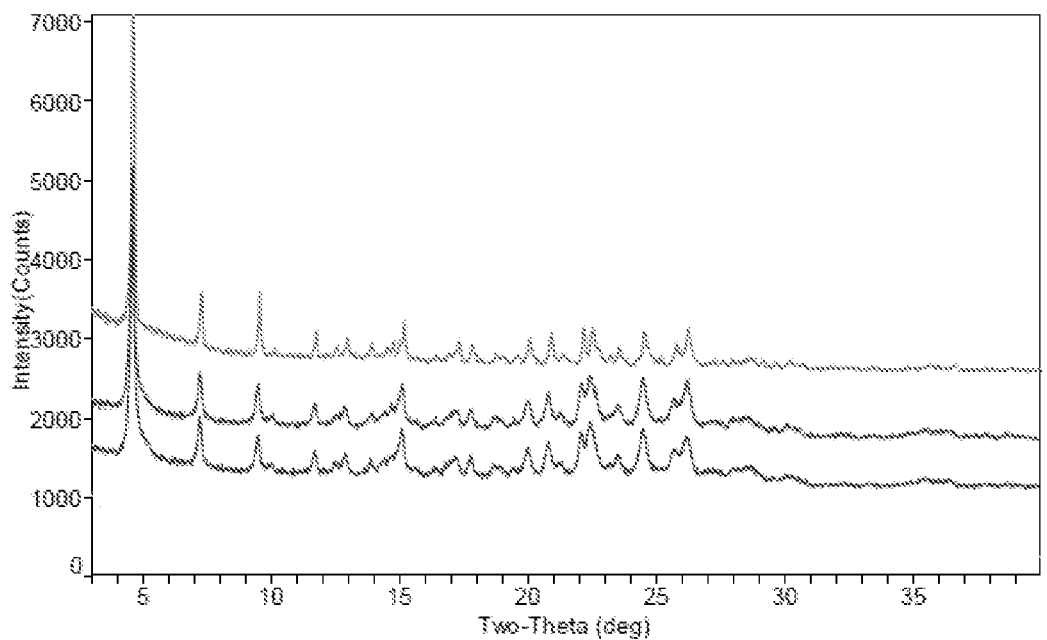
FIG. 8 is an X-ray powder diffraction pattern of the crystalline form II under tabletting conditions (from top to bottom: a crude sample, a sample after 25 kg pressure tabletting and a sample after 20 kg pressure tabletting)

The XRD of the obtained sample powder was compared with the XRD of the crude sample, the results are shown in FIG. 8 (from top to bottom: the crude sample, the sample after 25 kg pressure tabletting and the sample after 20 kg pressure tabletting). It turns out that the crystalline form II remains unchanged after tabletting.

Figure 9:
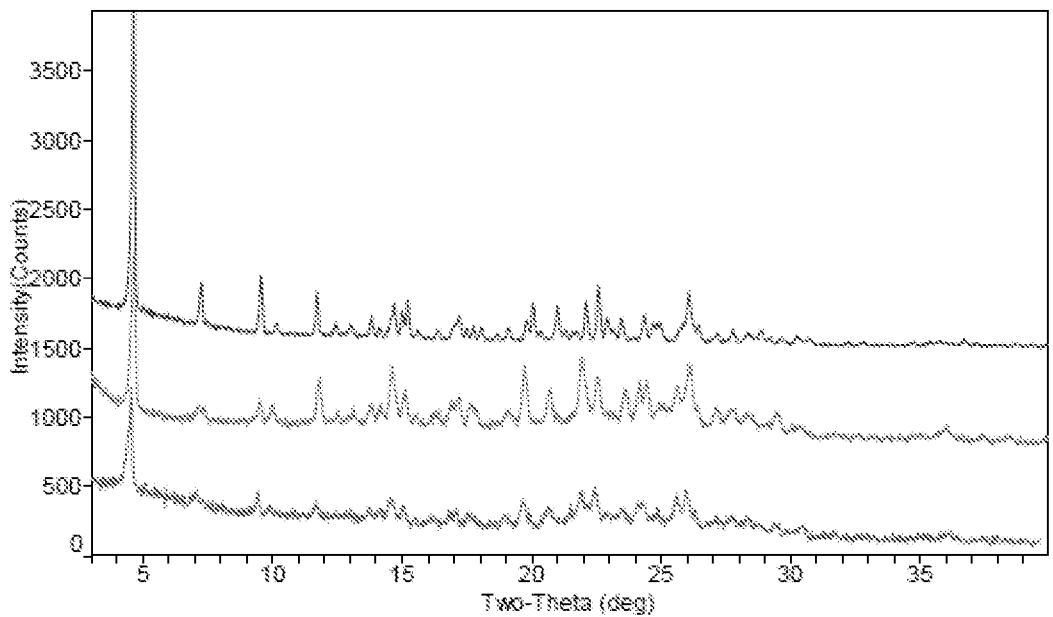
FIG. 9 is an X-ray powder diffraction pattern of crystalline form II after 10 days of high temperature and high humidity treating (from top to bottom: the crude sample, a sample at 60° C., a sample at 85% relative humidity)
Figure 10:
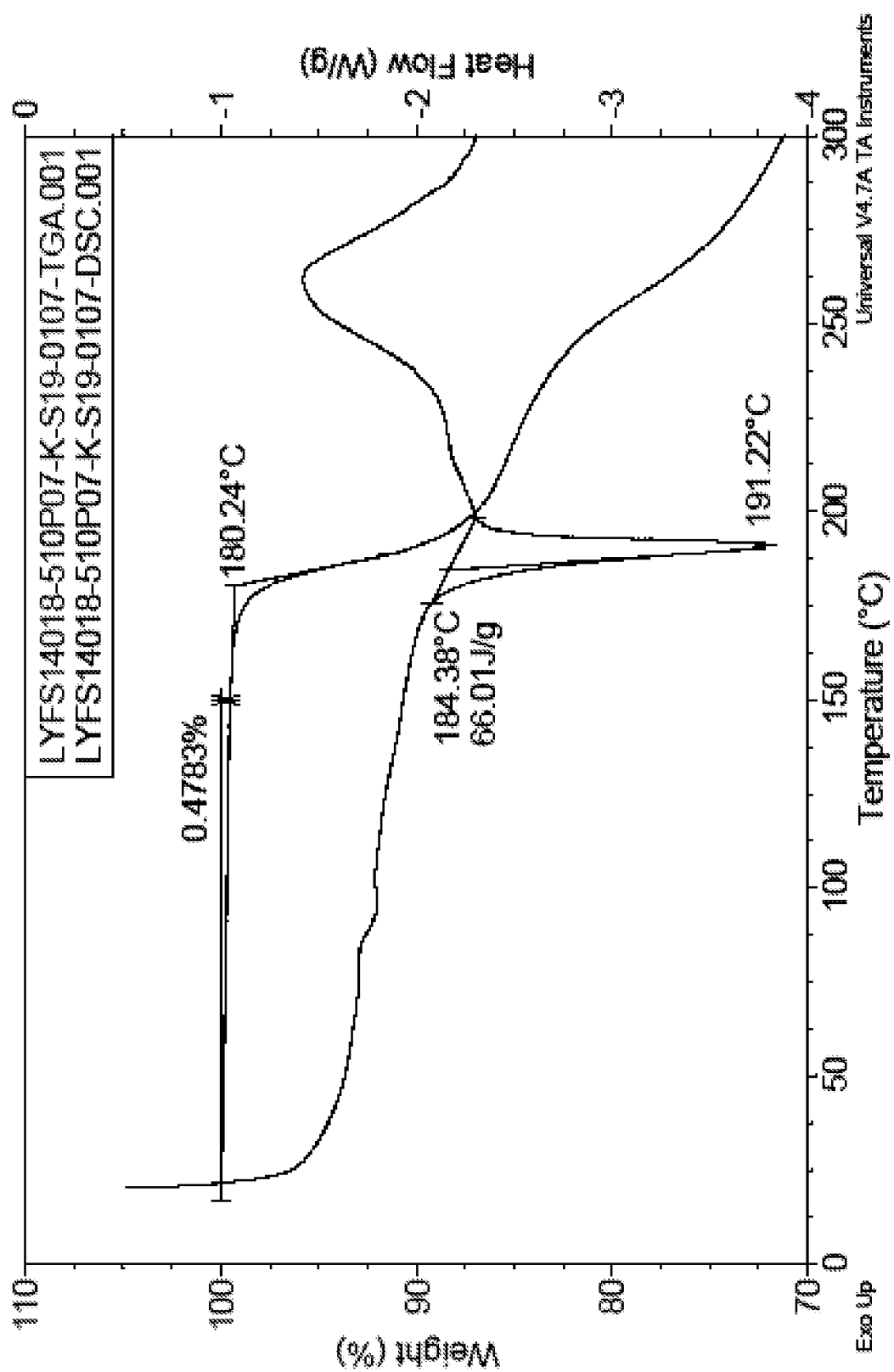
FIG. 10 is a DSC-TGA spectrum of the crystalline form I.
Figure 11:
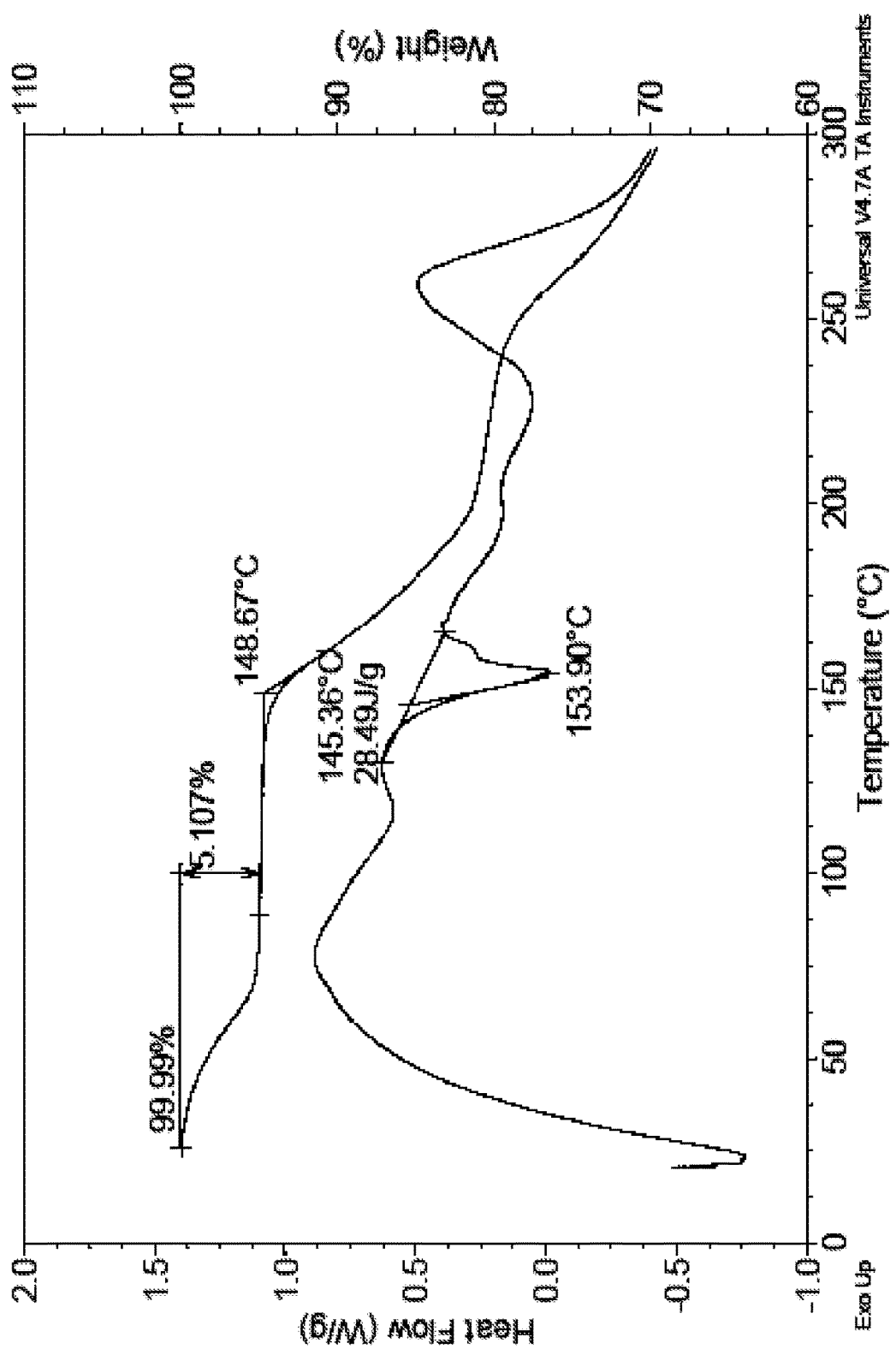
FIG. 11 is a DSC-TGA spectrum of the crystalline form II.
Figure 12:
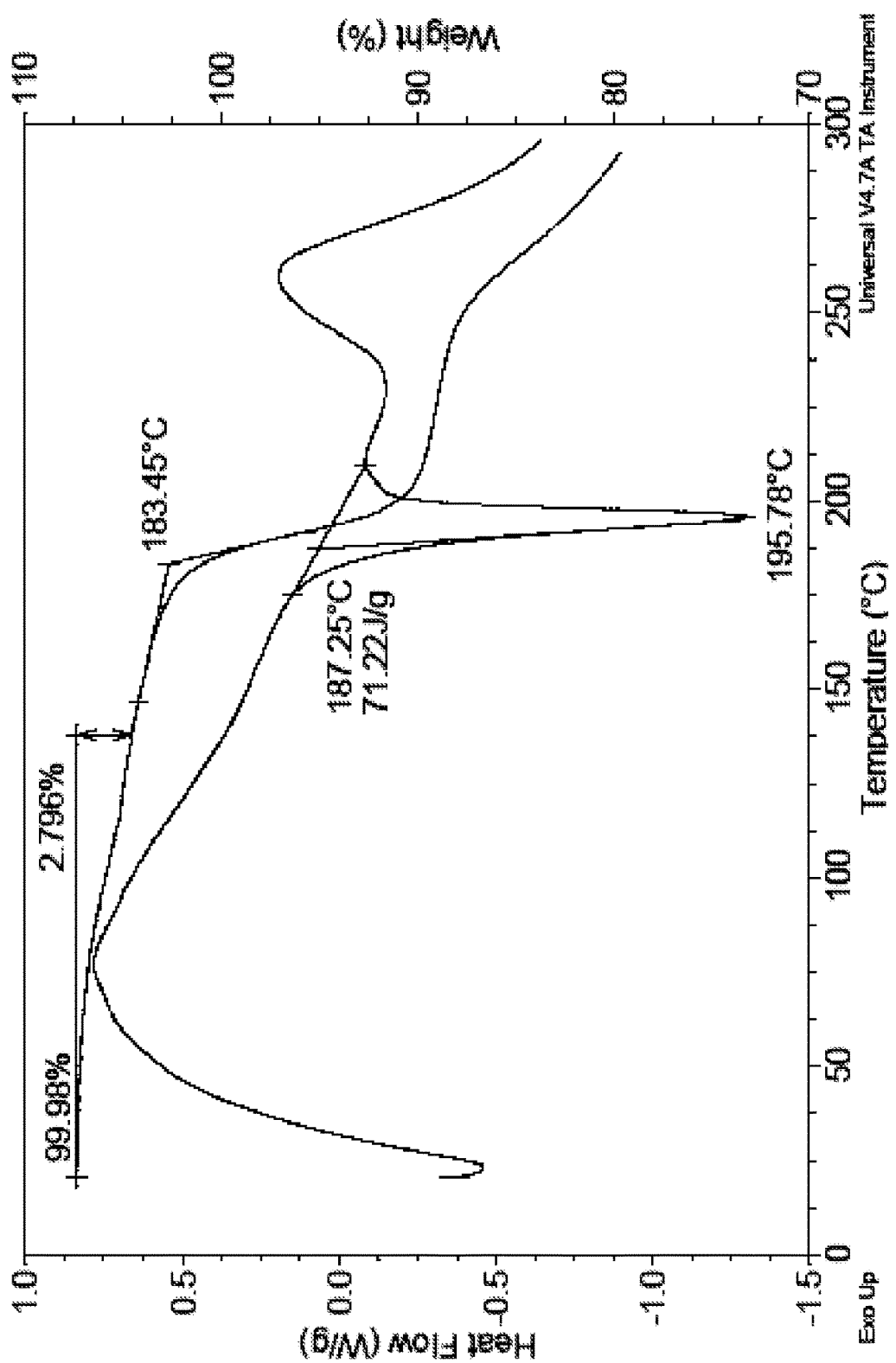
FIG. 12 is a DSC-TGA spectrum of the crystalline form III.
Figure 13:
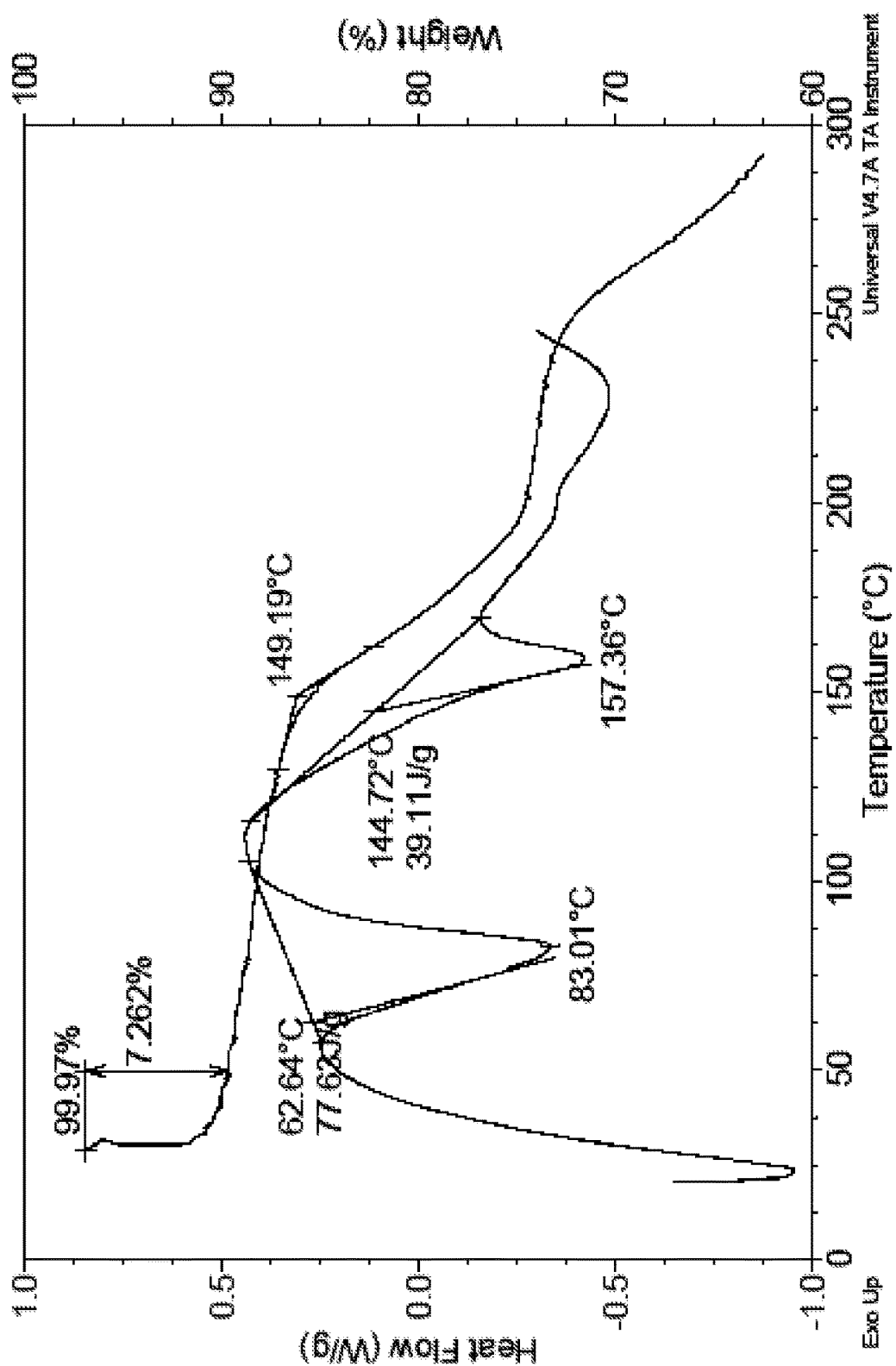
FIG. 13 is a DSC-TGA spectrum of the crystalline form IV.

Example 10: Investigating the Influences of High Temperature and High Humidity on the Crystalline Form II Two samples of 20 mg the crystalline form II were respectively placed at 60° C. (sealed and shielded from light) and 85% relative humidity (exposed in the air at room temperature and shielded from light), detected by XRD after 10 days and compared with XRD of the crude sample. It turns out that the crystalline form of the samples remains unchanged as shown in FIG. 9 (from top to bottom: the initial sample, the sample at 60° C. and the sample at 85% relative humidity).

Example 11: Comparative Stability Test

The stability of an amorphous form, the crystalline form I, a mixture of the crystalline form I and the crystal II, the crystal II, and the crystalline form III of the compound (A) was investigated. Specifically, the amorphous form, the crystalline form I, the mixture of the crystalline form I and the crystalline form II (weight ratio 1:2), the crystalline form II and the crystalline form III were taken 200 mg respectively to be investigated as follows:

Packing: Polyvinyl chloride (PVC) ziplock bag (the inner layer) was vacuumized, aluminum foil (the middle layer) was vacuumized, and aluminum foil desiccant (the outer layer) was vacuum and filled in with nitrogen;

Inspection conditions: 25° C., 60% relative humidity. The indicator was the total impurity content, which is determined by detection of samples three times at each time point with the average value recorded. The time points for sampling include 0, 1, 2, 3 and 6 months after packing. The test results are shown in Table 3 below.

TABLE 3

Comparative stability test

| objects of investigation | total impurity content % at different time (months) | | | | |
| --- | --- | --- | --- | --- | --- |
| | 0 | 1 | 2 | 3 | 6 |
| amorphous form | 1.52 | 13.28 | — | — | — |
| crystalline form I | 1.11 | 1.62 | 2.34 | 2.49 | 3.10 |
| mixture of crystalline form I and II | 0.90 | 1.58 | 2.20 | 2.40 | 3.29 |
| crystalline form II | 1.29 | 1.43 | 1.59 | 1.82 | 1.87 |
| crystalline form III | 1.56 | 2.55 | 2.98 | 3.34 | 3.76 |

It can be seen from the results of Table 3 that the chemical stability of the crystalline form I, the crystalline form II, the crystalline form III and the mixture of the crystalline form I or the crystalline form II is better than the amorphous form. Consequently, the crystalline forms of the compound (A) are more favorable to the quality control of drugs and drugability properties, compared with amorphous form.

Example 12: Comparative Pharmacokinetic Test

Drugs and reagents: The crystalline form I, the crystalline form II, the mixture of the crystalline form I and the crystalline form II (the weight ratio of the crystalline form I and the crystalline form II in the mixture thereof is 1:3), the crystalline form III and the amorphous form of the compound of formula (A) were employed as test samples in this study with purity of more than 99%, and sodium carboxymethylcellulose of pharmaceutical grade was employed as an excipient.

Test animals: SD rats were randomly divided into 6 groups. Each group has 6 animals, in which half male and half female.

Drug preparation: An appropriate volume of 0.5% (w/v) sodium carboxymethylcellulose aqueous solution was added to the samples according to the weight of each sample to make the final concentration of the drug 0.15 mg/ml, and each mixture was stirred under a magnetic stirrer for use.

Administration and sample collection: Each sample to be tested was intragastrically administered to a fasted SD rat at a dose of 10 ml/kg. 0.3 ml of blood was collected into the anti-coagulation tube of EDTA-K2 at 15 min, 30 min, 1 hour, 2 hours, 4 hours, 6 hours, 8 hours, 10 hours and 24 hours after administration, and centrifuged under 3000 g for 10 min at 4° C., with the supernatant taken and saved at −80° C. to be tested.

Compound (B) and azilsartan in the plasma of the samples were analyzed by LC-MS/MS (AB Sciex, API 3500 QTRAP). Compound (B) was not detected in the plasma of the animals sampled at each time point, since each test substance was rapidly converted into azilsartan in the animal body after administration. The pharmacokinetics parameters of azilsartan in the plasma of the animals after administration of the test substance are as follows:

| | AUClast (ng/mL * hr) | AUCINF (ng/mL * hr) | T½ (hr) | Cmax (ng/mL) | Tmax (hr) |
|---|---|---|---|---|---|
| crystalline form I | 17987 ± 4411 | 18606 ± 4994 | 7.29 ± 1.36 | 3410 ± 1195 | 0.46 ± 0.29 |
| crystalline form II | 19004 ± 4977 | 20972 ± 6525 | 7.72 ± 1.76 | 4138 ± 695 | 0.50 ± 0.00 |
| crystalline form III | 13042 ± 2865 | 14299 ± 2636 | 7.99 ± 2.57 | 3082 ± 767 | 0.25 ± 0.00 |
| mixture of crystalline form I and form II | 20709 ± 4263 | 22422 ± 5035 | 7.47 ± 0.88 | 4785 ± 675 | 0.50 ± 0.00 |
| amorphous | 9445 ± 3623 | 10419 ± 3649 | 7.89 ± 1.96 | 1955 ± 1445 | 0.46 ± 0.29 |

CONCLUSION in the above experiments, the crystalline forms or mixture of crystalline forms have good bioavailability, which are superior to the amorphous form.

The present application claims the priority of the Chinese Patent Application No. 201610539614.6 filed on Nov. 7, 2016, which is incorporated herein by reference as part of the disclosure of the present application.

What is claimed is:
1. A crystalline form of a compound of formula (A):

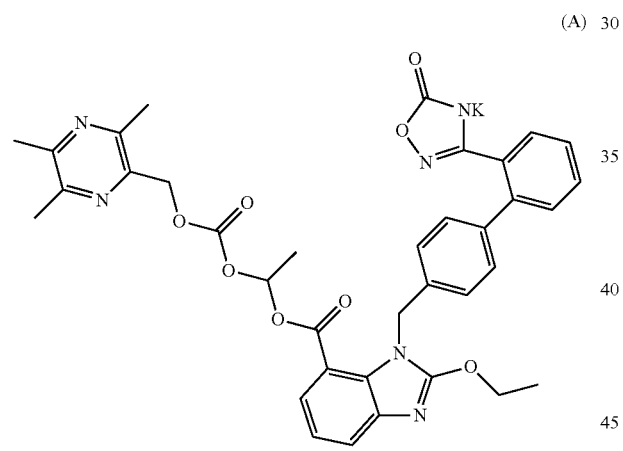

(A)

wherein the crystalline form comprises one or more chosen from a crystalline form I, a crystalline form II, a crystalline form III, or a crystalline form IV,
wherein an X-ray powder diffraction pattern of the crystalline form I comprises characteristic peaks at diffraction angles (2-Theta) of 5.3±0.2°, and 8.6±0.2°,
an X-ray powder diffraction pattern of the crystalline form II comprises characteristic peaks at diffraction angles (2-Theta) of 4.7±0.2°,
an X-ray powder diffraction pattern of the crystalline form III comprises characteristic peaks at diffraction angles (2-Theta) of 5.2±0.2° and 8.0±0.2°, and
an X-ray powder diffraction pattern of the crystalline form IV comprises characteristic peaks at diffraction angles (2-Theta) of 7.4±0.2°, 14.7±0.2°, and 16.0±0.2°.

2. The crystalline form according to claim 1, wherein a DSC spectrum of the crystalline form I shows a melting temperature at 184±5° C., a DSC spectrum of the crystalline form II shows a melting temperature at 145±5° C., a DSC spectrum of the crystalline form III shows a melting temperature at 187±5° C., and a DSC spectrum of the crystalline form IV shows a melting temperature at 145±5° C.

3. A preparation method of the crystalline form according to claim 1, wherein the crystalline form I is prepared by:
(1) adding a solvent to the compound of formula (A) to obtain a suspension, and then stirring at room temperature for 0.5 to 3 days to obtain the crystalline form I, wherein the solvent is one or more chosen from a mixture of ethanol and isopropyl ether, a mixture of ethanol and n-heptane, a mixture of isopropanol and n-heptane, or a mixture of tetrahydrofuran and n-heptane;
(2) dissolving the compound of formula (A) into a good solvent to obtain a clear solution, and adding an anti-solvent while stirring to obtain the crystalline form I, wherein the good solvent is one or more chosen from methanol, ethanol, or n-butanol, and the anti-solvent is one or more chosen from isopropyl ether, methyl tert-butyl ether, or methyl cyclohexane;
(3) dissolving the compound of formula (A) in a solvent under heating to a temperature at 40° C. to 90° C. to obtain a clear solution, and cooling the solution to obtain the crystalline form I, wherein the solvent is chosen from a mixture of ethanol and isopropyl ether, a mixture of ethanol and ethyl acetate, a mixture of ethanol and methyl tert-butyl ether, a mixture of ethanol and n-heptane, a mixture of ethanol and methylcyclohexane, or a mixture of n-butanol and n-heptane;
(4) placing the compound of formula (A) in a solvent atmosphere of ethanol for 1-3 days to obtain the crystalline form I; or
(5) adding the crystalline form III and/or the crystalline form IV of the compound of formula (A) into a solvent to form a suspension, stirring and drying to obtain the crystalline form I, wherein the solvent is an ester solvent chosen from ethyl acetate, isopropyl acetate, or a mixture thereof.

4. A preparation method of the crystalline form according to claim 1, wherein the crystalline form II is prepared by:
(1) dissolving the compound of formula (A) in a solvent to obtain a clear solution, evaporating the solution to dryness at room temperature to give the crystalline form II, wherein the solvent is chosen from a mixture of ethanol and ethyl acetate, a mixture of acetone and ethyl acetate, a mixture of acetone and isopropyl ether, or a mixture of acetone and n-heptane;
(2) adding the compound of formula (A) to a solvent to obtain a clear solution, a saturated solution, a supersaturated solution, or a suspension, and stirring at room temperature for 10 minutes to 5 days to obtain the crystalline form II, wherein the solvent is chosen from isopropanol, sec-butanol, ethyl acetate, toluene, isopropyl acetate, a mixture of ethanol and ethyl acetate, a mixture of ethanol and isopropyl acetate, a mixture of ethanol and toluene, a mixture of acetone and n-heptane, or a mixture of 1,4-dioxane and n-heptane;
(3) dissolving the compound of formula (A) in a good solvent to obtain a clear solution, and adding an anti-solvent under stirring to obtain the crystalline form II, wherein the good solvent is chosen from methyl ethyl ketone, dimethyl sulfoxide, or 1,4-dioxane, and the anti-solvent is chosen from n-heptane, isopropyl ether, or isopropyl acetate;
(4) dissolving the compound of formula (A) in a solvent under heating to a temperature of 40° C. to 90° C. to obtain a clear solution, and cooling the solution to obtain the crystalline form II, wherein the solvent is chosen from sec-butanol, nitromethane, acetone, or tetrahydrofuran;
(5) placing a saturated ethanol solution of the compound of the formula (A) in a solvent atmosphere of isopropyl ether or isopropyl acetate until the crystalline form II precipitates from the saturated ethanol solution; or
(6) placing the compound of formula (A) in a solvent atmosphere of toluene, isopropanol, tetrahydrofuran, or ethyl acetate for 1-3 days to obtain the crystalline form II.

5. A preparation method of the crystalline form according to claim 1, wherein the crystalline form III is prepared by:
(1) adding tetrahydrofuran to the compound of the formula (A) to obtain a suspension and stirring the suspension to at room temperature for 12 hours to 5 days obtain the crystalline form III; or
(2) placing a saturated tetrahydrofuran solution of the compound of formula (A) in a solvent atmosphere of isopropyl ether until the crystalline form III precipitates from the saturated solution.

6. A preparation method of the crystalline form according to claim 1, wherein the crystalline form IV is prepared by dissolving the compound of formula (A) in n-butanol to give a clear solution, and adding n-heptane under stirring to obtain the crystalline form IV.

7. A composition comprising the crystalline form I and the crystalline form II according to claim 1, wherein a weight ratio of the crystalline form I to the crystalline form II is from 1:99 to 99:1.

8. A preparation method of the composition according to claim 7, comprising:
(1) adding isopropyl acetate to the crystalline form II to obtain a suspension, and stirring at 50° C. to 90° C. for 3 hours to 3 days to obtain a mixture of the crystalline form I and the crystalline form II;
(2) pulverizing and sieving a wet product of the crystalline form II followed by vacuum drying at 40° C. to 60° C. for 3 hours to 3 days;
(3) vacuum drying a wet product of the crystalline form II at 40° C. to 60° C. for 3 hours to 3 days followed by micronizing; or
(4) adding a solvent to the crystalline form II to obtain a suspension, stirring the suspension at room temperature for 3 hours to 3 days to obtain a mixture of the crystalline form I and the crystalline form II, wherein the solvent is chosen from methyl tert-butyl ether or a mixture of ethanol and methylcyclohexane.

9. A pharmaceutical composition comprising a therapeutically effective amount of one, two, or more of the crystalline forms according to claim 1 and a pharmaceutically acceptable carrier; or a therapeutically effective amount of the composition according to claim 7 and a pharmaceutically acceptable carrier.

10. A method for prevention and/or treatment of hypertension, chronic heart failure, diabetic nephropathy, comprising:
preparing an angiotensin II receptor antagonist from a composition comprising one or more chosen from the crystalline forms I, II, III, IV, or a mixture thereof according to claim 1; and
administering the angiotensin II receptor antagonist or a medication comprising thereof to a subject in need thereof.

11. The preparation method of the crystalline form according to claim 2, wherein the crystalline form I is prepared by:
(1) adding a solvent to the compound of formula (A) to obtain a suspension, and then stirring at room temperature for 0.5 to 3 days to obtain the crystalline form I, wherein the solvent is one or more chosen from a mixture of ethanol and isopropyl ether, a mixture of ethanol and n-heptane, a mixture of isopropanol and n-heptane, or a mixture of tetrahydrofuran and n-heptane;
(2) dissolving the compound of formula (A) into a good solvent to obtain a clear solution, and adding an anti-solvent while stirring to obtain the crystalline form I, wherein the good solvent is one or more chosen from methanol, ethanol, or n-butanol, and the anti-solvent is one or more chosen from isopropyl ether, methyl tert-butyl ether, or methyl cyclohexane;
(3) dissolving the compound of formula (A) in a solvent under heating to a temperature at 40° C. to 90° C. to obtain a clear solution, and cooling the solution to obtain the crystalline form I, wherein the solvent is chosen from a mixture of ethanol and isopropyl ether, a mixture of ethanol and ethyl acetate, a mixture of ethanol and methyl tert-butyl ether, a mixture of ethanol and n-heptane, a mixture of ethanol and methylcyclohexane, or a mixture of n-butanol and n-heptane;
(4) placing the compound of formula (A) in a solvent atmosphere of ethanol for 1-3 days to obtain the crystalline form I; or
(5) adding the crystalline form III and/or the crystalline form IV of the compound of formula (A) into a solvent to form a suspension, stirring and drying to obtain the crystalline form I, wherein the solvent is an ester solvent chosen from ethyl acetate, isopropyl acetate, or a mixture thereof.

12. The preparation method of the crystalline form according to claim 2, wherein the crystalline form II is prepared by:
(1) dissolving the compound of formula (A) in a solvent to obtain a clear solution, evaporating the solution to dryness at room temperature to give the crystalline form II, wherein the solvent is chosen from a mixture of ethanol and ethyl acetate, a mixture of acetone and ethyl acetate, a mixture of acetone and isopropyl ether, or a mixture of acetone and n-heptane;
(2) adding the compound of formula (A) to a solvent to obtain a clear solution, a saturated solution, a supersaturated solution, or a suspension, and stirring at room temperature for 10 minutes to 5 days to obtain the crystalline form II, wherein the solvent is chosen from isopropanol, sec-butanol, ethyl acetate, toluene, isopropyl acetate, a mixture of ethanol and ethyl acetate, a mixture of ethanol and isopropyl acetate, a mixture of ethanol and toluene, a mixture of acetone and n-heptane, or a mixture of 1,4-dioxane and n-heptane;
(3) dissolving the compound of formula (A) in a good solvent to obtain a clear solution, and adding an anti-solvent under stirring to obtain the crystalline form II, wherein the good solvent is chosen from methyl ethyl ketone, dimethyl sulfoxide, or 1,4-dioxane, and the anti-solvent is chosen from n-heptane, isopropyl ether, or isopropyl acetate;
(4) dissolving the compound of formula (A) in a solvent under heating to a temperature of 40° C. to 90° C. to obtain a clear solution, and cooling the solution to obtain the crystalline form II, wherein the solvent is chosen from sec-butanol, nitromethane, acetone, or tetrahydrofuran;
(5) placing a saturated ethanol solution of the compound of the formula (A) in a solvent atmosphere of isopropyl ether or isopropyl acetate until the crystalline form II precipitates from the saturated ethanol solution; or
(6) placing the compound of formula (A) in a solvent atmosphere of toluene, isopropanol, tetrahydrofuran, or ethyl acetate for 1-3 days to obtain the crystalline form II.

13. The preparation method of the crystalline form according to claim 2, wherein the crystalline form III is prepared by:
(1) adding tetrahydrofuran to the compound of the formula (A) to obtain a suspension and stirring the suspension at room temperature for 12 hours to 5 days to obtain the crystalline form III; or
(2) placing a saturated tetrahydrofuran solution of the compound of formula (A) in a solvent atmosphere of isopropyl ether until the crystalline form III precipitates from the saturated solution.

14. The preparation method of the crystalline form according to claim 2, wherein the crystalline form IV is prepared by dissolving the compound of formula (A) in n-butanol to give a clear solution, and adding n-heptane under stirring to obtain the crystalline form IV.

15. A composition comprising one or more of the crystalline form I and the crystalline form II wherein a weight ratio of the crystalline form I to the crystalline form II is from 1:99 to 99:1.

16. A pharmaceutical composition comprising a therapeutically effective amount of one, two, or more of the crystalline forms according to claim 2, and a pharmaceutically acceptable carrier.

17. The crystalline form according to claim 1, wherein the X-ray powder
diffraction pattern of the crystalline form I further comprises characteristic peaks at diffraction angles (2-Theta) of 13.3±0.2°and 20.1±0.2°,
the X-ray powder diffraction pattern of the crystalline form II further comprises characteristic peaks at diffraction angles (2-Theta) of 7.3±0.2°, 9.6±0.2°, 15.2±0.2°, and 26.3±0.2°,
the X-ray powder diffraction pattern of the crystalline form III further comprises characteristic peaks at diffraction angles (2-Theta) of 12.4±0.2°, and 13.6±0.2°, and
the X-ray powder diffraction pattern of the crystalline form IV further comprises characteristic peaks at diffraction angles (2-Theta) of 8.4±0.2°, 22.6±0.2°, 23.2±0.2°, and 29.7±0.2°.

18. The crystalline form according to claim 17, wherein the X-ray powder diffraction pattern of the crystalline form I further comprises characteristic peaks at diffraction angles (2-Theta) of 6.3±0.2°, 10.6±0.2°, and 26.3±0.2°;
the X-ray powder diffraction pattern of the crystalline form II further comprises characteristic peaks at diffraction angles (2-Theta) of 11.8±0.2°and 24.6±0.2°,
the X-ray powder diffraction pattern of the crystalline form III further comprises characteristic peaks at diffraction angles (2-Theta) of 19.2±0.2°, and
the X-ray powder diffraction pattern of the crystalline form IV further comprise characteristic peaks at diffraction angles (2-Theta) of 24.0±0.2°.

19. The crystalline form according to claim 18, wherein the X-ray powder diffraction pattern of the crystalline form I further comprises characteristic peaks at diffraction angles (2-Theta) of 12.7±0.2°,
the X-ray powder diffraction pattern of the crystalline form II further comprises characteristic peaks at diffraction angles (2-Theta) of 22.6±0.2°, and
the X-ray powder diffraction pattern of the crystalline form III further comprises characteristic peaks at diffraction angles (2-Theta) of 10.3±0.2°, 12.2±0.2°, and 21.4±0.2°.

20. The crystalline form of claim 1, wherein the X-ray powder diffraction pattern of the crystalline form I comprises characteristic peaks at diffraction angles (2-Theta) substantially as shown in FIG. 1,
the X-ray powder diffraction pattern of the crystalline form II comprises characteristic peaks at diffraction angles (2-Theta) substantially as shown in FIG. 2,
the X-ray powder diffraction pattern of the crystalline form III comprises characteristic peaks at diffraction angles (2-Theta) substantially as shown in FIG. 3; and
the X-ray powder diffraction pattern of the crystalline form IV comprises characteristic peaks at diffraction angles (2-Theta) substantially as shown in FIG. 4.

* * * * *